United States Patent
Aquino Olivos et al.

(10) Patent No.: US 9,410,935 B2
(45) Date of Patent: Aug. 9, 2016

(54) MEASUREMENT PROCESS OF MINIMUM MISCIBILITY PRESSURE (MMP) AND CRITICAL POINTS OF A GAS IN CRUDE OILS OR BINARY MIXTURES

(71) Applicant: INSTITUTO MEXICANO DEL PETROLEO, Mexico City (MX)

(72) Inventors: Marco Antonio Aquino Olivos, Mexico City (MX); Adriana de Jesus Aguirre Gutierrez, Mexico City (MX); Jose Luis Mendoza de la Cruz, Mexico City (MX); Sergio Alvarez Badillo, Mexico City (MX)

(73) Assignee: INSTITUTO MEXICANO DEL PETROLEO, Mexico City (MX)

( * ) Notice: Subject to any disclaimer, the term of this patent is extended or adjusted under 35 U.S.C. 154(b) by 0 days.

(21) Appl. No.: 14/711,385

(22) Filed: May 13, 2015

(65) Prior Publication Data
US 2015/0330962 A1    Nov. 19, 2015

(30) Foreign Application Priority Data
May 14, 2014  (MX) .................... MX/a/2014/005812

(51) Int. Cl.
*E21B 47/06*     (2012.01)
*G01N 33/28*     (2006.01)
(Continued)

(52) U.S. Cl.
CPC ............... *G01N 33/28* (2013.01); *E21B 47/06* (2013.01); *G01N 25/4873* (2013.01); *G01N 33/2823* (2013.01); *E21B 43/25* (2013.01); *G01N 25/00* (2013.01); *Y10T 436/214* (2015.01)

(58) Field of Classification Search
CPC ... G01N 33/2823; G01N 33/28; G01N 25/00; G01N 33/26; G01N 25/02; G01N 25/4873; E21B 47/06; E21B 43/25; E21B 49/08; G01L 7/18; G01L 9/00; Y10T 436/214
See application file for complete search history.

(56) References Cited

U.S. PATENT DOCUMENTS

| | | | |
|---|---|---|---|
| 4,455,860 A | 6/1984 | Cullick et al. | |
| 4,621,522 A | 11/1986 | Christiansen et al. | |

(Continued)

FOREIGN PATENT DOCUMENTS

| | | |
|---|---|---|
| FR | 1253235 | 1/1961 |
| GB | 858270 | 1/1961 |

OTHER PUBLICATIONS

Alvarez-Badillo, S. et al., 14th International Conference on Petroleum Phase Behavior and Fouling, Jun. 10-13, 2013, Rueil Malmaison, France, Oral Jun. 12, 2013, "OF2—C02 Minimum Pressure by Scanning Transitiometry".*

(Continued)

*Primary Examiner* — Jennifer Wecker
(74) *Attorney, Agent, or Firm* — Dickinson Wright PLLC (57) ABSTRACT

The present invention provides a new process of the transitiometric scanning technique to determine in an experimental way the minimum miscibility pressure of any sample of hydrocarbon at constant temperature (from the atmospheric temperature to 673 K) in the pressure interval of the atmospheric temperature to 400 MPa, including pressure at which the organic matter will precipitate due to the $CO_2$ injection, based on a transitometric technique which has proved to be reliable, highly accurate and highly reproducible. The apparatus used is based on a highly accurate control of the pVT variables and the calorimetric determination of the present phase transitions during the injection process of gases into hydrocarbons. Accurate control of pVT variables enables the determination of the derivative thermodynamic variables useful to define the type of phase transition.

4 Claims, 6 Drawing Sheets

(51) Int. Cl.
  E21B 49/08 (2006.01)
  G01N 25/02 (2006.01)
  G01L 7/18 (2006.01)
  G01N 25/48 (2006.01)
  *G01N 33/26* (2006.01)
  *E21B 43/25* (2006.01)
  *G01L 9/00* (2006.01)
  *G01N 25/00* (2006.01)

(56) References Cited

U.S. PATENT DOCUMENTS

| | | |
|---|---|---|
| 4,627,273 A | 12/1986 | Christiansen et al. |
| 5,505,074 A | 4/1996 | Mihcakan et al. |
| 6,750,062 B1 | 6/2004 | Randzio et al. |
| 7,779,672 B2 | 8/2010 | Robin |
| 2015/0060057 A1* | 3/2015 | Hawthorne ............ E21B 43/25 166/250.01 |
| 2015/0092816 A1 | 4/2015 | Grolier et al. |

OTHER PUBLICATIONS

Alvarez-Badillo, S. et al., 14th International Conference on Petroleum Phase Behavior and Fouling, Jun. 10-13, 2013, Rueil Malmaison, France, Oral Jun. 12, OF2—CO2 Minimum Pressure by Scanning Transitiometry.

* cited by examiner

MEASUREMENT PROCESS OF MINIMUM MISCIBILITY PRESSURE (MMP) AND CRITICAL POINTS OF A GAS IN CRUDE OILS OR BINARY MIXTURES

CROSS-REFERENCE TO RELATED APPLICATION

This application claims the benefit and priority under 35 U.S.C. §119 to Mexican Patent Application No. MX/a/2014/005812 with a filing date of May 14, 2014, the disclosure of which is incorporated herein by reference in its entirety.

FIELD OF THE INVENTION

This invention relates to a process for experimental determination of the minimum miscibility pressure (MMP) of the carbon dioxide in any type of hydrocarbon oil having a specific gravity range from 25 to 10° API, a temperature of 339.55 to 427.15 K, and the MMP of the binary mixture n-decane+$CO_2$ for temperature from 310.93 and 344.28 K and pressures up to 20 MPa. In the case of dead crude oil, the pressure at which the precipitation of the organic matter begins for $CO_2$ injection is based on a scan transitometer equipment.

BACKGROUND OF THE INVENTION

An important design consideration in enhanced oil recovery (EOR) processes is the determination of the conditions under which the dynamic miscibility may be reached for certain fluids and specific characteristics in a reserve. Temperature of the process is established by the reserve conditions but the pressure may be controlled within certain limits. Likewise, the injected gas composition may also be controlled. Therefore, the problem is only with the determination of the minimum miscibility pressure.

As its name indicates, the MMP is the minimum pressure at which the injection of a gas ($CO_2$ or other gas) reaches its miscibility upon multiple contacts with crude oil for specific composition and temperature (Stalkup, 1984; Green and Willhite, 1998; Pedersen and Christensen, 2007).

Usually, the MMP for gas/oil mixtures has been measured by means of displacement experiments in a slim tube (Yellig and Metcalfe, 1980), the rising bubble apparatus (Christinasen, et al. 1986, 1987) and the technique of vanishing the interfacial tension (Rao, 1997). These experiments involve the oil contact by means of a gas at constant temperature (reservoir temperature, $T_{res}$) evaluating the dissolvent potential used for the oil recovery. The slim tube experiments are also made to determine the effects of gas injection speed, composition of both gas and oil in the displacement system and on recovery efficiently. Although the experiments to measure the MMP in the slim tube (Yellig and Metcalfe, 1980) are considered as standard in the oil industry, there is no standardized apparatus, process or criteria to determine the MMP with this technique. In addition to these disadvantages, the slim tube technique is extremely time consuming (4-5 weeks), requires the use of a lots of fluid (crude oil and injection gases), cleaning thereof among experiments with different oils is also extremely time consuming and solvents (xylene, toluene, dichloromethane, nitrogen, etc.) and, if organic matter precipitation occurs (asphaltenes), the precipitates may cover the packing pores and damage the slim tube, thus rendering it unusable.

U.S. Pat. No. 4,455,860 discloses an apparatus and method for determination of $CO_2$ MMP of a reservoir oil. This apparatus is comprised of a capillary tube which is filled with crude oil at specific pressure (lower than the MMP and the reservoir temperature). The technique describes the injection of $CO_2$ at a constant flow and the measurement of the pressure drop between the entrance and exit of the tube, where the experiment is repeated at different pressures. MMP value is inferred by the behavior during the pressure drop between the experimental values and the values calculated by the Hagen-Poiseuille equation under the same temperature and pressure conditions.

U.S. Pat. No. 4,627,273 relates to the apparatus and the rising bubble technique to measure the MMP of a gas in a liquid. The apparatus is basically comprised of a steel sight gauge which contains a cylindrical transparent tube resistant to pressure used to hold and to observe the flow of the fluids in question and a needle at the bottom thereof, this needle is used for injection of the displacement gas. The process for determination of the MMP consists of filling in the cylinder by the bottom part of the tube with distilled water at the intended pressure, then, crude oil is injected through the upper part of the tube so that the water is displaced, when the cylinder has been filled with oil, a gas bubble is formed in the bottom part of the tube. The buoyant force of the bubble causes its rising through the oil and the MMP is determined by the shape and color of the rising bubbles. The test is made at different pressures until finding the MMP, pressure under which the bubble vanishes due to the effect of the multiple contact with oils before reaching the upper part of the tube.

U.S. Pat. No. 4,621,522 relates to a method to determine the minimum enhancement an injection gas should have to reach the miscibility with the liquid hydrocarbon by observing the behavior of the bubbles rising by a cylindrical tube. It is partially related to a continuation-in-part of U.S. Pat. No. 4,627,273.

U.S. Pat. No. 5,505,074 relates to an apparatus and a method to determine the minimum miscibility pressure (MMP) of a gas in a liquid based on the pressure changes regarding the time in a rising bubble apparatus.

Another apparatus and technique used for determining the MMP is the technique of vanishing the interfacial tension (VIT) developed by Rao (1997). The apparatus to determine the MMP with the technique of vanishing the interfacial tension consists of a stainless steel sight gauge operating up to 70 MPa and 473 K. The sight gauge has two glass windows placed on the opposite sides enabling observation and collection of images profiles of the drop/bubble using a light source on one side and a camera system on the opposite side. The cameras are connected to a high resolution monitor and to a computer equipped with an image collection port and imaging analysis software. As well as with an axial drops symmetry analysis (ASDA) software interactively calculating the IFT. Equation used for the IFT calculation requires density values of the liquid and gas phases which are measured with a vibrating tube densimeter and they are calculated with a commercial simulator based on a compositional analysis of the gas phase, respectively.

U.S. Pat. No. 7,779,672 discloses a method and an apparatus to measure the minimum miscibility pressure between two phases for enhanced recovery processes or geologic storage of $CO_2$. The method is based on the technique of vanishing the interfacial tension initially reported by Rao (1997) but making such technique faster and more independent from the measurement of densities of the liquid and gaseous phases.

Song et al. (2011) recently developed a technique to determine the minimum miscibility pressure of the n-decane+$CO_2$ system. Based on a magnetic resonance imaging study, data obtained by this technique showed results comparable to the results of the technique developed by Rao (1997), to the results of Ayirala (2005) and to the results obtained by the rising bubble technique and the slim tube technique (Elsharkawy, 1996). One of the disadvantages of the magnetic resonance imaging is that the images obtained from the phases corresponding to the miscibility pressure are extrapolated to a zero value in the intensity of the signal and as in the technique of vanishing the interfacial tension, the MMP correspond to an extrapolation of a very good description of the behavior of a property regarding the pressure. In addition, no experiments for crude oil samples are reported.

Despite the above-mentioned techniques exist, most of the measurements of the MMP have certain disadvantages, among which the following may be found: extremely time consuming, high operation costs, use of great sample amounts, measurements are strongly subject to interpretation that the experimenter provides, (slim tube apparatus) since there are no standardized criteria or processes. Results are not based on any thermodynamic criteria (rising bubble apparatus) or the value reported from the MMP is an extrapolation (technique of vanishing the interfacial tension) of a good description of the property up to certain limit inherent to the apparatus. Therefore, an apparatus and a suitable technique are required for determination of the MMP under different temperature and pressure conditions for any type of hydrocarbon.

French patent application No. FR 1253235 discloses the application of the transitiometric technique for the oil industry. A process of fluid charge in a calorimetric cell is described in the patent. The patent discloses the application for determining transition from liquid to solid, liquid to steam and solid to liquid phases for crude oil of any concentration in a wide interval of temperature and pressure; the above to determine the surrounding precipitation of asphaltenes of any kind of oil. The French patent is a key background for this invention, which is hereby incorporated by reference in its entirety.

SUMMARY OF THE INVENTION

The present invention is directed to a process where it is possible to measure the MMP between $CO_2$ and hydrocarbons as well as critical points for binary mixture n-decane+ $CO_2$ in a wide range of temperature, pressure and gravity ° API. In addition, before making measurements of MMP, the point under which precipitation of organic matter, such as asphaltenes, occurs may be determined, due to the change in composition by injection of $CO_2$.

Critical point is the limit under which the liquid and steam concentrations are the same. The term dead oil is used for oil that does not have dissolved gas at sufficiently low pressure, it does not have dissolved gas remaining or that does not release its volatile components. The live crude oil is oil that contains dissolved gas in solution and can be released under surface conditions. Live oil must be manipulated under strictly controlled conditions to prevent explosion or fire. Finally, the residual or remaining gas is the gas found in the reserve after the different explosion phases but that remains in the reserve and the amount of gas contained in solution is much less than that of live oil.

The present invention determines the MMP based on a novel technology such as the transitiometry which enables accurate measurements of the pressure, temperature and volume thermodynamic variables and the heat changes induced by a variable known as from the time.

The invention is directed to a process for the measurement of the minimum miscibility pressure (MMP) and critical points of gas in crude oil and binary mixtures of n-decane and carbon dioxide. The crude oil can be alive, residual and/or dead. The process uses a transitiometer system having a calorimeter with a measurement cell and a reference cell. In a first phase, the transitiometer is dried and cleaned and evacuated with a vacuum pump to remove remaining gases, such as air or $N_2$. The transitiometer is then filled with mercury by gravity and pressurized to at least 80 MPa. The pressure is then reduced to at least 7 MPa and the temperature is adjusted to the desired temperature. A crude oil sample is introduced into the measurement cell and $CO_2$ is injected by a pump. The thermal and mechanic variables are monitored for pressure (p), volume (V) and the calorimetric signal. In a second phase of the process, the isothermal compressibility $K_T$ [$MPa^{-1}$] is used to detect a change of the asymptotic behavior. The temperature can range from room temperature to 673K and the pressure can range from atmospheric to 400 MPa. The process is able to determine the beginning of asphaltene in the mixture. The test sample can range from 0.5 cc until 20 cc with a reproducibility level of 100%. The calorimetric signals and pressure signals by the process of the invention are presented in graphs as shown in FIGS. 2-7. The changes in the graphs are used as an indicator to determine the MMP for the sample.

BRIEF DESCRIPTION OF DRAWINGS

A brief description of the drawings is provided to have better understanding of the process known by the applicant for measurement of the minimum miscibility pressure (MMP) and critical points without limiting its scope:

FIG. 7 shows the multi contact miscibility process observed between the crude oil and the $CO_2$. In the same way, it is observed that the behavior of the isothermal compressibility corresponds to a series of fluctuations due to gas incorporation in the liquid until reaching the MMP indicated with an arrow at 14.46 MPa pressure, in this point of the curve the calorimetric signal has a gradient change due to the phase transition.

DETAILED DESCRIPTION OF THE INVENTION

This invention is directed to process for measurement of the minimum miscibility pressure (MMP) of the $CO_2$ of any kind of dead and residual oil (or remaining oil) in the specific gravity interval of 10 at 34° API at different temperatures (up to 427.15 K) and up to 100 MPa, including pressure at which the organic matter precipitates (asphaltenes) by $CO_2$ injection and the critical points of the binary mixture $CO_2$+n-decane, from 7 up to 19 MPa and the temperature range from 310.93 to 472.26 K.

The apparatus with which the measurements were taken is a scan transitiometer by scanning transitiometry which combines a calorimeter with a highly accurate control in the pressure variables p, temperature T and volume V, and the heat changes induced by a time based known variable. Main characteristics of this experimental equipment are the following:

The transitiomer includes a calorimetric block having two detectors and the variable volume cells are introduced therein. One cell is used to hold the sample under study and the other as reference cell. Each calorimetric detector includes six hundred and twenty-two (622) temperature sensors combined in series and cylindrically arranged so that they can detect the heat signal with high sensibility. Pressure is operated with a step motor by means of a control software. The device to measure the pressure is a Viatran 245 transducer operating at 400 MPa and it has a 0.15% measurement uncertainty in the total scale.

Digital acquisition of temperature has a $4\times10^{-4}$ K resolution. Temperature detectors are platinum thermometers Pt100 placed between the reference cell and the measurement cell. Accuracy of isothermal measurements is ±0.05 K and in scan mode in temperature of ±0.1 K.

Pressure sensors, step motor, temperature controls and calorimetric amplifier are connected to a digital control module. Software of this equipment allows controlling and recording the pressure p variables, T temperature, volume V and heat q flow, being language software (Virtual Instrument) LabView VI. These four variables may be simultaneously monitored during all the experiment process (U.S. Pat. No. 6,750,062, which is hereby incorporated by reference in its entirety).

Figure 1:
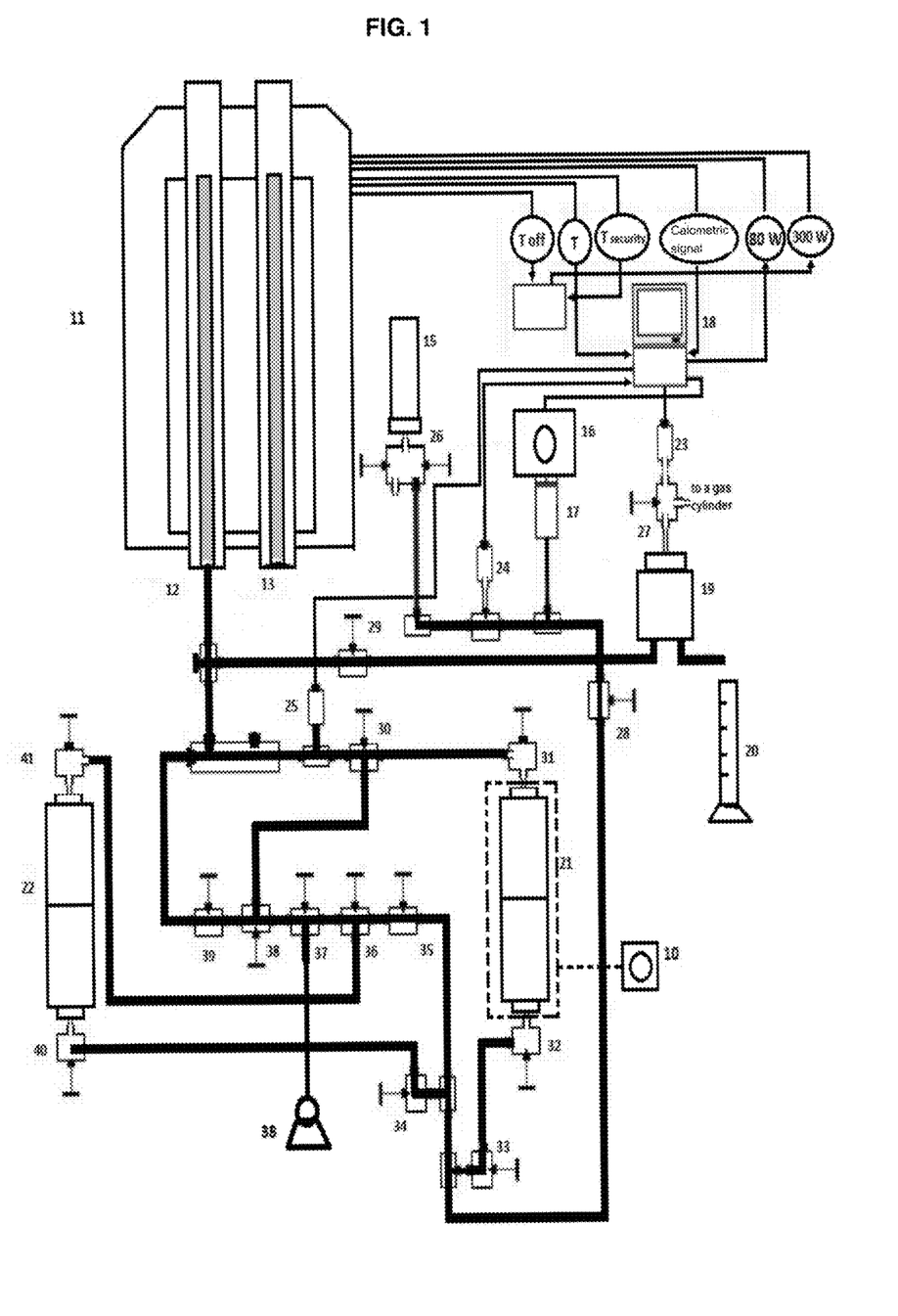
FIG. 1 generally shows a transitiometer scheme used in this invention.

As shown in FIG. 1, the transitiometer includes a calorimeter block 11, wherein two variable volume twin cells are introduced, a measurement cell 12, in which phase transitions measurements are performed and a reference cell 13. Pump 17, controlled by a step motor 16, used for displacement of fluids under study throughout the piping, which are located in the high pressure cylinders 21 and 22, to produce pressure in the system which is registered with three pressure transducers 23 (Dynisco, PT4604-15M-6), 24 and 25 (Viatran 245), and that can be controlled by means of a back pressure regulator 19 (BPR) which works as a flow valve. A related apparatus is also disclosed in commonly owned U.S. Patent Publication No. 2015/0092816, which is hereby incorporated by reference in its entirety Basic principle for determining the transition of phases of any substance or mixture of substances has been studied in detail and it has shown to be effective, capable of being reproduced and highly accurate (Randzio, 1996, 1997; Aquino-Olivos et al., 2010 and 2013). The apparatus is based on a calorimetric principle and a highly accurate control of pVT variables throughout the measurement.

MMP measurement, specifically a dead oil sample and $CO_2$ as injection gas is performed at the reserve temperature ($T_{yac}$), which is in the measurement limits of the transitometric system, i.e., $T_{amb}<=T_{yac}<=400°$ C. y $P_{atm}<=P_{yac}<=60000$ lb/in². Once the crude oil sample is charged in the calorimetric cell (Stage 1) and it is stabilized at the reserve temperature of the sample, a determined calculated volume of $CO_2$ is injected under supercritical conditions (T=311 K and p=8 MPa). $CO_2$ injection in the oil sinus is performed by forced convection. The related thermodynamic Pvt variables are monitored and controlled throughout the measurement process as well as the calorimetric signal. Once the gas and liquid mixture is in the cell and they are thermally stable, pressure is produced in the measurement cell by means of a pump controlled by the step motor. During the pressurization process, the $CO_2$ vaporizes the light components of the oil, thus creating a multiple contact mixing process between the gas and the oil. The pVT variables, derivative property (isothermal compressibility) and the calorimetric signal are monitored during the mixing process until all variables suffer a last change in their behavior; this change is shown in the calorimetric signal as a change in the curve slope of this variable and in the isothermal compressibility as the last sudden change, corresponding to the incorporation of the last gas bubble which has been enriched by the oil during multiple contact between both, thus producing a single miscible phase. Pressure corresponding to the changes both on the calorimetric signal and the isothermal compressibility corresponds to the minimum miscibility pressure.

Regarding the pressure at which the organic matter precipitates (asphaltenes), this point was determined by the constant injection of $CO_2$ into the calorimetric cell at reserve temperature and pressure ($T_{yac}$ and $P_{yac}$) of the corresponding oil. A constant determined calculated volume of $CO_2$ was injected into the oil previously introduced in the cell. During the constant injection of $CO_2$ the constant pressure of the system was maintained by means of a back pressure regulator. No change of phase corresponding to the organic matter precipitation was noted. Once sufficient gas was injected at reserve pressure, the valve of the backpressure regulator was closed so that the injection of gas increased the pressure in the system until finding the pressure at which the calorimetric signal and the first pressure derivate regarding the volume would have a considerable change. This change may not be observed in the isothermal compressibility since at those conditions, the gas and the oil are a homogenous mixture.

Regarding the determination of the critical points of the binary mixture n-decane+$CO_2$, the process to determine the phase transition of the two phases region to the single phase region was the following: (i) a determined amount of n-decane was charged into the system, once the hydrocarbon was in the cell the temperature was established and was expected to be constant, (ii) $CO_2$ was constantly injected by means of a pump controlled by the step motor under supercritical conditions. During the $CO_2$ injection in the n-decane sinus, the calorimetric signal and the pVT variables of the system were monitored until the resulting mixture passed from two phases to a single phase. Criteria applied for determination of the critical point of the n-decane+$CO_2$ mixture was the isothermal compressibility since this thermodynamic variable has the characteristic of presenting a very particular behavior in the phase transition corresponding to the critical region, such behavior is presented as a sudden change or as an asymptotic behavior in the critical point of the mixture. In addition to the isothermal compressibility, changes in the calorimetric signal and in the pVT of the binary mixture are observed.

EXAMPLES

To obtain reliable measurements of the interested variables, it was necessary to calibrate the temperature, pressure and volume sensors and validate the miscibility measurements among the phases with the binary n-decane+$CO_2$ system since this system has been used as a standard system to represent the miscibility between the hydrocarbon and $CO_2$ as injection gas.

The following example illustrates the process to determine the miscibility between the n-decane and the carbon dioxide at two different temperatures 310.93 and 344.26 K.

Example 1

Minimum Miscibility Pressure for $CO_2$+n-Decane System (Binary System) at 310.93 K and 344.28 K Process was performed for determining the MMP for the $CO_2$+n-decane system at 310.93 K. The process is described in two phases:

Phase 1 charge of system and Phase 2 results analysis.

Before starting with the experimental measurements, the system of FIG. 1 (piping, high pressure cell and valves) was washed with dichloromethane and nitrogen dried This process was repeated three times to guarantee no traces of oil or solvents remain from a previous study.

Phase 1. Once the measurement system is clean and dried, the whole system is evacuated with a vacuum pump 38 to remove remaining gases (air or $N_2$).

Upon completion of the degassing of the system, the system is filled with the mercury contained in the reservoir 15 by means of gravity. Then, the equipment is pressurized with pump 17 controlled by the step motor 16 to approximately 80 MPa so that leaks due to pressure drop may be detected in the transitometric system. Then the system's pressure is reduced until charge pressure above 7 MPa.

Calorimetric block 11 is set in the measurement position and the high pressure cells 12 and 13 are located therein and the system temperature is set at 310.93 K by means of the control and monitoring program in LabView. When the temperature is reached and stable, the n-decane in the high pressure cylinder 22 is transferred displacing 2 mL of n-decane by means of the pump 17 controlled by the step motor 16. Charge of n-decane into the calorimetric cell is performed by displacing the mercury which acts as a piston fluid to transport the n-decane. The mercury which has been displaced is recovered in a burette 20 upon exit from the back pressure regulator 19.

Once presence of the alkane is observed in the calorimetric cell, $CO_2$ is injected which is contained in a high pressure cylinder 21 temperature controlled by a rheostat 10. To inject the $CO_2$ into the cell containing alkane, the same process as for n-decane is applied.

Gas injection is in the alkane sinus in such a way that a mixture of substances is produced by forced convection. The process is performed by monitoring at all times the thermal and mechanical variables of the process. Process continues until observing changes in the behavior of variables pV and in the calorimetric cell.

Figure 2A:
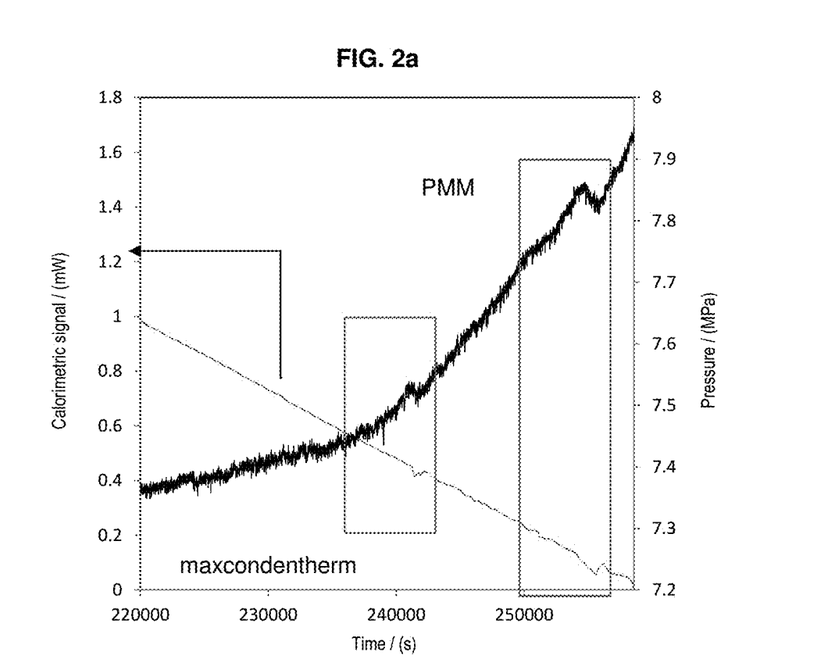
FIGS. 2a and 2b present the injection process of $CO_2$ to a sample of n-decane, behaviour of the calorimetric signal and pressure based on the time at a 310.93 K temperature. Two phase transitions framed by rectangles are shown in FIG. 2a, the first one corresponding to a maxcondentherm (maximum temperature under which the mixture coexists in two phases L-V) and the second rectangle corresponding to the MMP measured by the transitiometry technique or scanning transitiometry method. An approach to the MMP region is shown in FIG. 2b where the phase transition both in the calorimetric signal and in the pressure is observed.

Phase 2. As observed in FIGS. 2 and 3 to determine the type of phase transition, causing the changes in the variables pV and in the calorimetric signal, isothermal compressibility is used, which is a derivative thermodynamic property which has a very particular behavior in the MMP region. This behavior is described as a "sudden change" or an asymptotic behavior of the property. All thermodynamic and transportation properties showing singularities in the critical region or total miscibility are directly related to the isothermal compressibility. Therefore, it is used as fundamental thermodynamic criteria to verify that the phase transition corresponding to the MMP has been reached. FIG. 2(a) shows the behavior of the calorimetric signal regarding the time (continuous line) and FIG. 2(b) indicates the behavior of the pressure regarding the experimentation time (small circles).

The process described in FIG. 2(a) corresponds to the phase transition to determine the MMP. It is observed in FIG. 2(a) that approximately at 7.53 MPa there is a change in the curves slope corresponding to the calorimetric signal and to the pressure, such point implies to be corresponding to a maxcondentherm, such as it is reported by Reamer and Sage (1963). After this change, other phase transition is observed at 7.86 MPa pressure corresponding to the MMP value reported by various authors using different experimental techniques, pVT cells (Reamer and Sage, 1963), slim tube apparatus and rising bubble apparatus (Elsharwaky et al., 1996) and the technique of vanishing the interfacial tension (Ayirala and Rao, 2006).

Figure 2B:
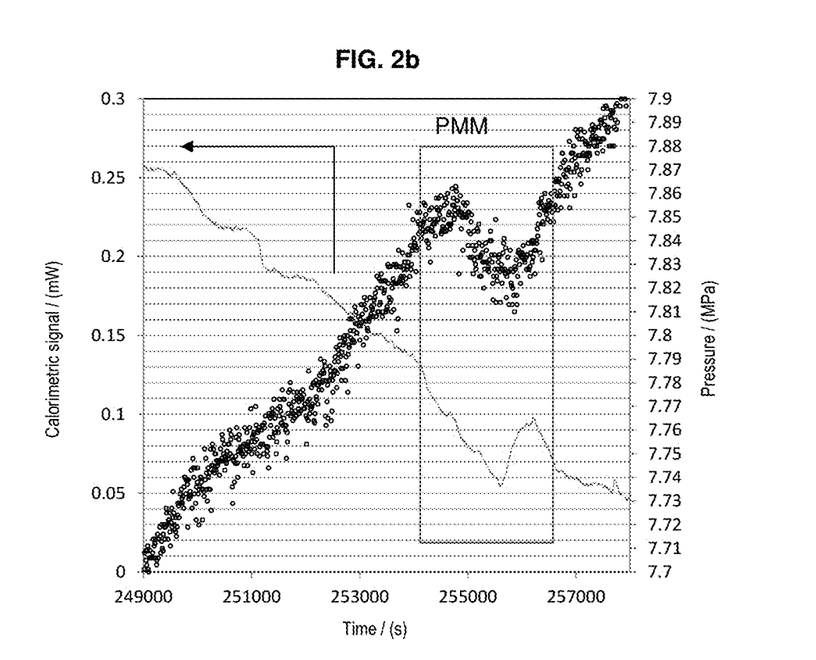

The FIG. 2(b) graph presents an approach to the MMP region wherein the phase transition may be observed both in the calorimetric signal and in the pressure.

Figure 3:
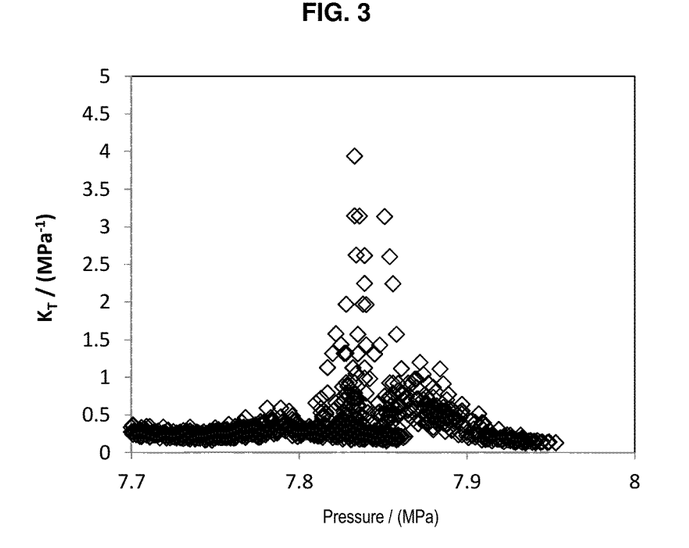
FIG. 3 describes the behavior of the isothermal compressibility represented as $K_T$ [$MPa^{-1}$], based on the pressure, showing the region where the MMP is reached between the $CO_2$ and the n-decane at a temperature of 310.93 K. A sudden jump is observed in the behavior of the property in the MMP region, such as thermodynamics of the balance between the phases balance suggests.

FIG. 3 shows the isothermal compressibility behavior regarding the pressure. It is observed that there is a sudden change at 7.84 MPa pressure in the isothermal compressibility values corresponding to the MMP. At 310.93 K temperature, the solubility of the n-decane in $CO_2$ is low.

The same process as described in Phases 1 and 2, corresponding to the charge of the transitometric system and to the construction of the data was performed for the isothermal of 344.28 K.

Figure 4:
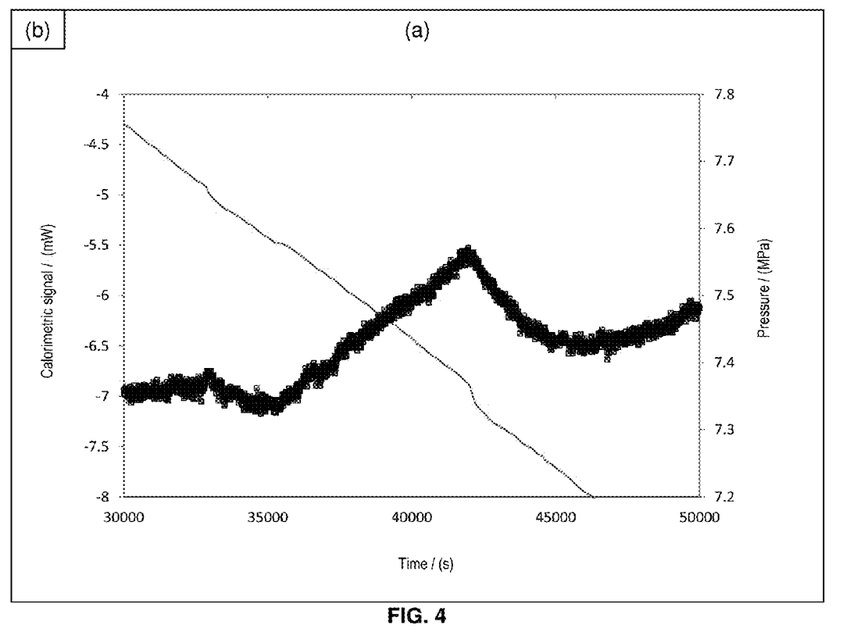
FIG. 4 shows the injection process of $CO_2$ to a n-decane sample wherein the behaviour of the calorimetric signal and pressure are under a temperature of 344.28 K. Two phase transitions are observed in the graph a), the first phase corresponds to the transition of the $CO_2$ at supercritical fluid, the second phase corresponds to a maxcondentherm. The critical point of the mixture is observed in graph b), variables p and the calorimetric signal are observed affected by the phase transition.

FIG. 4 shows the behavior of the calorimetric signal and the system pressure regarding the measurement time. This Figure is divided into two parts, two phase transitions are observed in item a), the first corresponds to the phase transition of the $CO_2$ into a supercritical fluid, value obtained is comparable to that reported by Ambrose (1992), second phase transition observed corresponds to the reported by Reamer and Sage (1963) as a maxcondentherm at 7.56 MPa pressure. Two phase transitions are observed as changes in the thermal response and mechanics of the equipment behavior.

Figure 5:
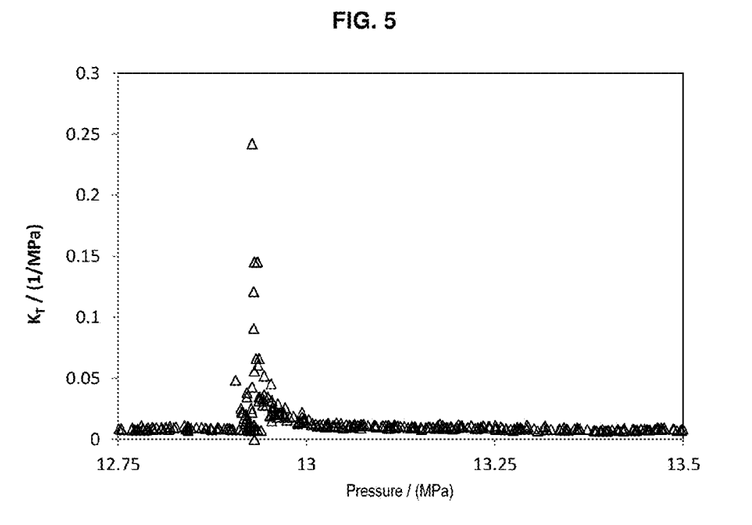
FIG. 5 shows the isothermal compressibility behavior in the region wherein the critical point between $CO_2$ and the n-decane is reached at a temperature of 344.28 K. A sudden jump in the behavior of the property is observed in the region of the critical point, such as it is suggested by the thermodynamics of balance between phases. It is also observed that the compressibility curve is better defined since the $CO_2$ is more alkane soluble at 344.28 K.

FIG. 5 shows the isothermal compressibility curve regarding the pressure, where an asymptotic behavior is clearly observed at 12.9 MPa pressure. Isothermal compressibility curve is better defined for temperature 344.28 K (FIG. 5) than for isothermal 310.93 K (FIG. 3). This occurs because the alkane solubility in the $CO_2$ increases regarding the temperature increase, such as the balance data liquid-steam suggest reported by different authors (Reamer and Sage, 1963; Nagarajan and Robinson, 1986).

Example 2

Determination of the Pressure at which the Organic Matter Precipitates by $CO_2$ Injection in Dead Oil Process by means of which it was determined if the $CO_2$ injection in dead oil promotes the precipitation of the organic matter (asphaltenes) is according to Phase 1 of Example 1. Only the n-decane by the dead crude oil is substituted in the description made in the above-stated example.

After the constant injection of a $CO_2$ volume higher than the oil volume injected under pressure and the reserve temperature, it is observed in the mechanical and thermal variables if the asphaltenes precipitation is presented. Otherwise, valve 29 is closed in such a way that the $CO_2$ injection increases the pressure in the system until reaching a pressure at which the organic matter precipitates.

Figure 6:
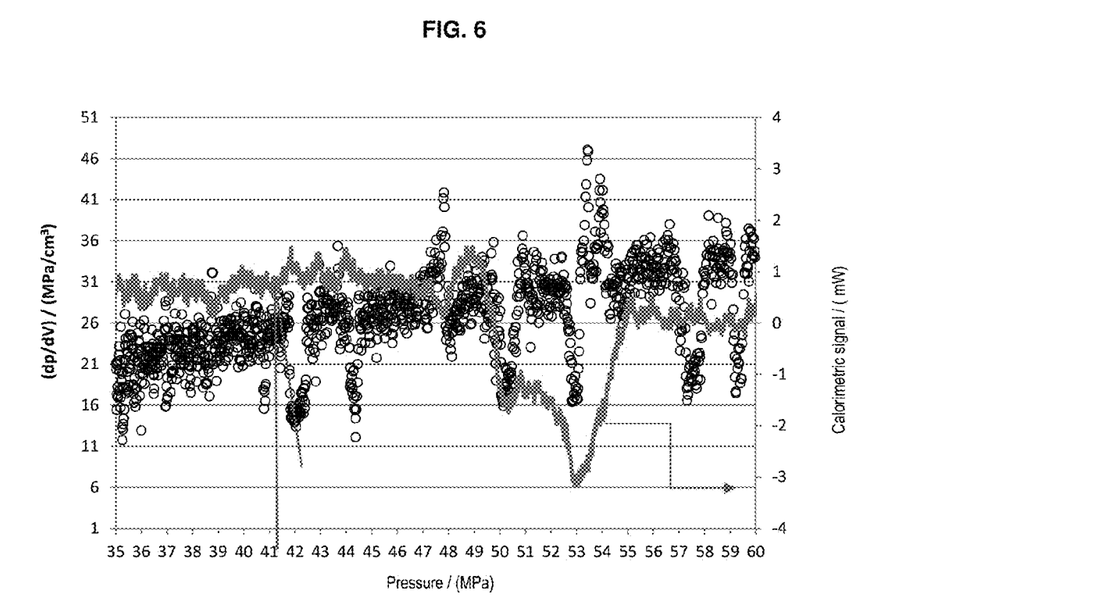
FIG. 6 shows the behavior of the calorimetric signal and the dp/dV derivative regarding pressure, it is observed that the precipitation of organic matter begins at 41.4 MPa and the kinetics of the addition thereof by the $CO_2$ injection occurs not until reaching 47 MPa.

FIG. 6 shows the curve of the calorimetric signal and the first pressure derivative regarding the volume (dp/dV) in a graphic versus the system pressure. It is observed that the calorimetric signal suffers a change in the slope at 41.4 MPa pressure that corresponds to changes in the behavior of the first derivative. These changes are referred to the beginning of organic matter precipitation for the $CO_2$ injection.

Example 3

Minimum Miscibility Pressure for Dead Oil Under Reserve Conditions

Process for determining the MMP of dead oil is according to the description of Phase 1 of Example 1. Once the $CO_2$ is detected in the calorimetric cell 12 and that the intended volume of $CO_2$ has been injected, valve 29 connected to the BPR 19 is closed in such a way there is increase in the system pressure until detecting the MMP.

Criteria applied to determine the MMP of $CO_2$ in the dead oil correspond to the criteria applied in Example 1, namely, the mechanical and thermal response provided by the equipment based on the calorimetric signal and pVT behavior and the derivative thermodynamic properties such as the isothermal compressibility.

Figure 7:
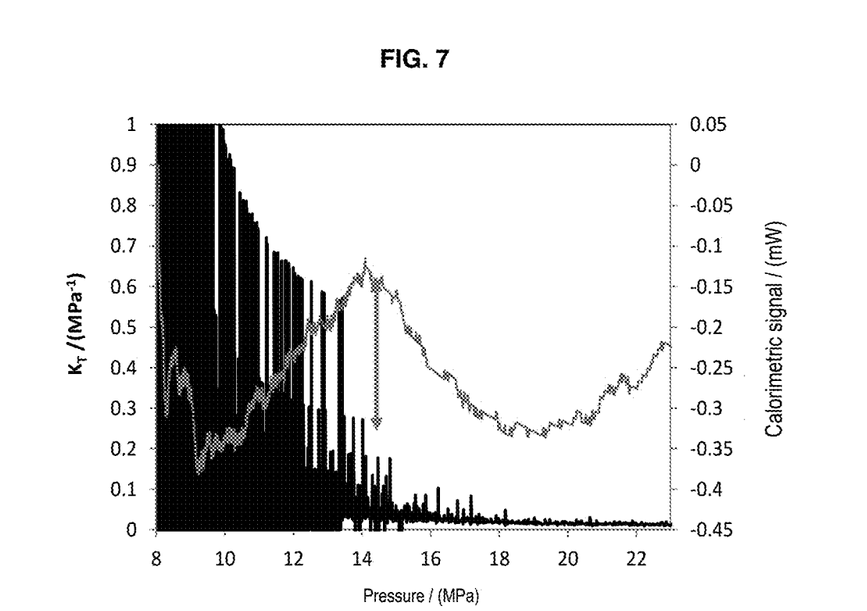

The graph of the behaviour of the calorimetric signal and isothermal compressibility regarding the pressure is shown in FIG. 7. It is observed that the isothermal compressibility behaves like a decreasing bar graph. This behavior is due to the mass transference process produced by multiple contact occurring between gas and oil. As to what regards the calorimetric signal, the curve presents a series of fluctuations caused, as above-stated by the mixture process and increase of pressure until reaching the MMP corresponding to the point indicated with an arrow in FIG. 7 in the value 14.46 MPa.

What is claimed is:

1. A process for the measurement of the minimum miscibility pressure (MMP) and critical points of a gas in crude oil or binary mixtures wherein the crude oil is alive, residual and/or dead, wherein said process comprises two phases, phase 1: a) with a dried and clean transitiometer system, evacuating all the system with a vacuum pump to remove remaining gases (air or N2); b) upon completion of the system degassing, and filling the system with mercury by gravity; c) pressurizing the system at 80 MPa; d) once step (c) is completed, reducing the charge pressure until approximately 7 MPa; e) adjusting the system temperature to the desired temperature; f) transferring the crude oil sample to be analyzed to a measurement cell, once presence is detected in a calorimetric cell, proceeding to inject $CO_2$ by means a transitiometer pump; g) monitoring the thermal and mechanic variables p, V and the calorimetric signal; and phase 2: a) using isothermal compressibility KT [$MPa^{-1}$] to detect a change in the asymptotic behavior of the property.

2. The measurement process according to claim 1, wherein a pressure of the system ranges from atmospheric pressure to 400 MPa and a temperature interval of the system ranges from room temperature to 673 K.

3. The measurement process according to claim 1, wherein before measuring MMP the beginning of asphaltene precipitation in the live mixture is determined, due to the change in composition by injection of $CO_2$.

4. The measurement process according to claim 1, wherein the volume of the crude oil sample is between 0.5 cc to 20 cc, with a reproducibility level of 100%.

* * * * *